United States Patent [19]

Maurer et al.

[11] 4,382,947
[45] May 10, 1983

[54] COMBATING PESTS WITH N-METHYL-CARBAMIC ACID O-PYRAZOL-4-YL ESTERS

[75] Inventors: Fritz Maurer, Wuppertal; Ingeborg Hammann, Cologne; Bernhard Homeyer, Leverkusen; Wolfgang Behrenz, Overath, all of Fed. Rep. of Germany

[73] Assignee: Bayer Aktiengesellschaft, Leverkusen, Fed. Rep. of Germany

[21] Appl. No.: 319,767

[22] Filed: Nov. 9, 1981

Related U.S. Application Data

[63] Continuation of Ser. No. 167,556, Jul. 11, 1980, abandoned.

[30] Foreign Application Priority Data

Jul. 31, 1979 [DE] Fed. Rep. of Germany ....... 2931033

[51] Int. Cl.³ .................. A01N 43/56; C07D 231/18
[52] U.S. Cl. ................... 424/273 P; 548/375; 548/377
[58] Field of Search .................. 548/375, 377; 424/273 P

[56] References Cited

U.S. PATENT DOCUMENTS 2,681,915  6/1954  Gysin .................... 548/377

FOREIGN PATENT DOCUMENTS 414249  12/1966  Switzerland ............... 548/377

*Primary Examiner*—Henry R. Jiles
*Assistant Examiner*—Natalia Harkaway
*Attorney, Agent, or Firm*—Sprung, Horn, Kramer & Woods

[57] ABSTRACT

N-Methyl-carbamic acid O-pyrazol-4-yl esters of the formula

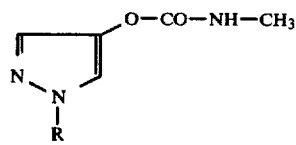

in which R is optionally substituted alkyl, alkenyl, alkynyl, cycloalkyl or phenyl, which possess insecticidal, acaricidal and nematicidal properties.

9 Claims, No Drawings

COMBATING PESTS WITH N-METHYL-CARBAMIC ACID O-PYRAZOL-4-YL ESTERS

This is a continuation of application Ser. No. 167,556, filed July 11, 1980, now abandoned.

The invention relates to certain new N-methyl-carbamic acid O-pyrazol-4-yl esters, to a process for their preparation and to their use as agents for combating pests, especially as insecticides, acaricides and nematicides.

It is known that certain carbamic acid esters, for example, N,N-dimethyl-carbamic acid O-(1-isopropyl-3-methylpyrazol-5-yl) ester, N-methyl-carbamic acid O-(2-isopropoxyphenyl) ester and N-methyl-carbamic acid O-(2,3-dihydro-2,2-dimethyl-7-benzofuranyl) ester, have a pesticidal action (see Swiss Pat. No. 282,655, DE-AS (German Published Specification) No. 1,108,202 and U.S. Pat. No. 3,474,171). However, the action of these compounds is not always completely satisfactory, especially in the case of low concentrations of active compound and when small amounts are applied.

The present invention now provides, as new compounds, the N-methyl-carbamic acid O-pyrazol-4-yl esters of the general formula

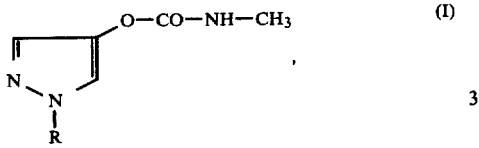

in which R represents an optionally substituted alkyl, alkenyl, alkynyl, cycloalkyl or phenyl radical.

Preferred compounds of the formula (I) are those in which R represents straight-chain or branched alkyl, alkenyl, alkinyl or alkoxyalkyl with up to 4 carbon atoms, cycloalkyl with 3 to 6 carbon atoms or phenyl.

Surprisingly, the compounds of the formula (I) according to the invention display a considerably more powerful insecticidal, acaricidal and nematicidal action than known compounds of similar structure and the same type of action.

The invention also provides a process for the preparation of a carbamic acid ester of the formula (I) in which a 4-hydroxypyrazole of the general formula

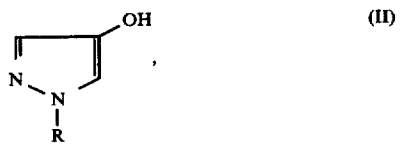

in which R has the meaning indicated above, is carbamoylated. This can be effected in the customary manner.

If, for example, 1-cyclobutyl-4-hydroxy-pyrazole and methyl isocyanate are used as starting substances, the reaction of these compounds can be outlined by the following equation:

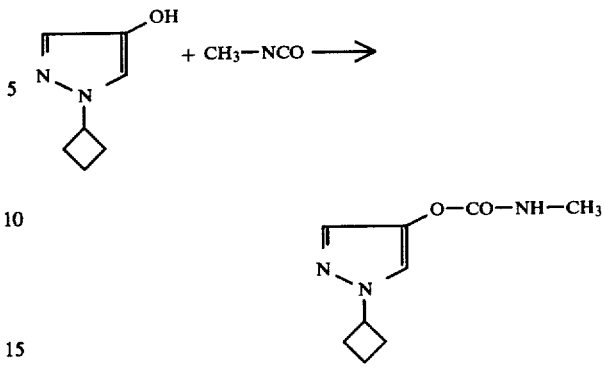

Formula (II) provides a definition of the 4-hydroxypyrazoles to be used as starting substances. Preferably, in this formula, R represents straight-chain or branched alkyl with 1 to 4 carbon atoms or cycloalkyl with 3 to 6 carbon atoms.

Examples of the compounds (II) which may be mentioned are: 1-methyl-, 1-ethyl-, 1-n-propyl-, 1-iso-propyl-, 1-n-butyl-, 1-iso-butyl-, 1-sec.-butyl-, 1-tert.-butyl-, 1-cyclopropyl-, 1-cyclobutyl-, 1-cyclopentyl- and 1-cyclohexyl-4-hydroxy-pyrazole.

4-Hydroxy-pyrazoles of the formula (II) are known (see Liebigs Ann. Chem. 313 (1900), 17). The compounds (II) are obtained, for example, by reacting 4-methoxy-pyrazoles with hydrobromic acid. The 4-methoxy-pyrazoles are prepared in a known manner from hydrazines and 2-methoxy-4-dimethylamino-acrolein (see Archiv der Pharmazie 300 (1967), 704–708).

Methyl isocyanate, which can be used as a further starting compound, is known.

The process for the preparation of the N-methyl-carbamic acid O-pyrazol-4-yl esters according to the invention is preferably carried out using a suitable solvent or diluent. Possible solvents or diluents are virtually any of the inert organic solvents. These include, as preferences, aliphatic and aromatic, optionally chlorinated hydrocarbons, such as benzine, benzene, toluene, xylene, methylene chloride, chloroform, carbon tetrachloride, chlorobenzene and o-dichlorobenzene; ethers, such as diethyl ether, dibutyl ether, tetrahydrofuran and dioxane; ketones, such as acetone, methyl ethyl ketone, methyl isopropyl ketone and methyl isobutyl ketone; and nitriles, such as acetonitrile and propionitrile.

If appropriate, the preparative process is carried out using a catalyst. Catalysts which can be used here are, in particular, aliphatic, aromatic or heterocyclic amines, for example triethylamine, trimethylamine, dimethylaniline, dimethylbenzylamine, pyridine, diazabicyclooctane, diazabicyclononene and diazabicycloundecene.

The reaction temperature can be varied within a substantial range. In general, the reaction is carried out between 0° and 100° C., preferably between 10° and 80° C.

The process is in general carried out under normal pressure. For carrying out the process according to the invention, between 1 and 1.5 moles, preferably between 1 and 1.2 mols of methyl isocyanate are usually employed per mol of 4-hydroxy-pyrazole of the formula (II). The reaction is preferably carried out using one of the above-mentioned catalysts in one of the diluents indicated above. The reaction mixture is stirred at the required temperature for several hours. The solvent is then distilled off in vacuo. The products are thereby obtained in an oily or crystalline form. They are characterized by their melting points or their refractive indexes.

Other carbamoylation processes would be the reaction of a compound (II) with phosgene and subsequent reaction of the resulting compound with methylamine, or the reaction of a compound (II) with ω-methylcarbamic acid chloride.

As already mentioned, the N-methyl-carbamic acid O-pyrazol-4-yl esters according to the invention are distinguished by an outstanding insecticidal, acaricidal and nematicidal activity. They have a low phytotoxicity and are active against plant pests as well as against pests harmful to health and pests of stored products. The compounds according to the invention can thus successfully be employed as agents for combating pests in the protection of plants and the protection of stored products and in the hygiene field.

The active compounds are well tolerated by plants, have a favorable level of toxicity to warm-blooded animals, and can be used for combating arthropod pests, especially insects and acarids, and nematode pests which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Gelleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Cryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio moliter,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodores spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichodorus spp.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.0001 to 1% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The active compounds according to the invention are also suitable for combating ectoparasites and endoparasites in the field of veterinary medicine.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides pesticidal composition containing as active ingredient a compound of the present invention in admixture with a solid or liquefied gaseous diluent or carrier or in admixture with a liquid diluent or carrier containing a surface-active agent.

The present invention also provides a method of combating pests (especially arthropods, in particular insects or acarids, and nematodes) which comprises applying to the pests, or to a habitat thereof, a compound of the present invention alone or in the form of a composition containing as active ingredient a compound of the present invention in admixture with a diluent or carrier.

The present invention also provides a method of freeing or protecting domesticated animals from parasites which comprises applying to said animals a compound according to the present invention, in admixture with a diluent or carrier.

The present invention further provides crops protected from damage by pests by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasites by the application to said animals of a compound according to the present invention, in admixture with a diluent or carrier.

PREPARATIVE EXAMPLES

Example 1

(a) The 4-methoxypyrazoles, some of which are known, which are employed as precursors for the 4-hydroxypyrazoles could be prepared, for example, as follows:

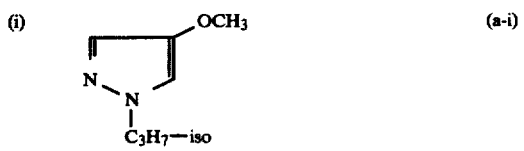

A mixture of 129 g (1 mol) of 2-methoxy-3-dimethylaminoacrolein (for the preparation, see Archiv der Pharmazie 300 (1967), pages 704–708), 123 g (1 mol) of isopropylhyrazine hemi-sulphate and a solution of 1.1 mols of sodium methylate 400 ml of methanol was boiled under reflux for 24 hours. The solvent was then distilled off in vacuo, 500 ml of water were added to the residue and the mixture was then extracted with 1 liter of chloroform. The organic solution was washed with 500 ml of water, dried over sodium sulphate and then evaporated at 30° C. in vacuo. The residue was distilled in vacuo and 82.5 g (60% of theory) of 1-isopropyl-4-methoxy-pyrazole were thus obtained in the form of a yellow oil with a boiling point of 94°–96° C./14 mm Hg.

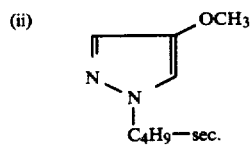
(ii) (a-ii)

A mixture of 23.6 g (0.21 mol) of potassium tert.-butylate, 19.6 g (0.2 mol) of 4-methoxypyrazole (for the preparation, see Archiv der Pharmazie 300 (1967), pages 704–708), 100 ml of tetrahydrofuran and 28.7 g (0.21 mol) of sec.-butyl bromide was stirred at 70° C. for 18 hours. 300 ml of water were then added and the mixture was extracted 3 times with 100 ml of chloroform each time. The combined organic phases were dried over sodium sulphate and evaporated in vacuo. 13.2 g (42% of theory) of 1-sec.-butyl-4-methoxypyrazole were obtained from the residue, by vacuum distillation, in the form of a colorless oil with a boiling point of 60° C./0.2 mm Hg.

The following compounds of the formula

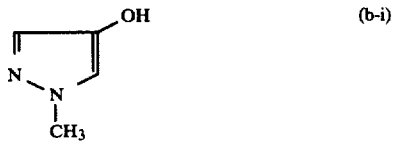

could be prepared analogously to (a-i) or (a-ii)

| Ether Intermediate No. | R | Yield (% of theory) | Refractive index; boiling point (°C./mm Hg) |
|---|---|---|---|
| a-iii | CH₃ | 80 | 72–74/7 |
| a-iv | C₂H₅ | 54 | 90–93/14 |
| a-v | C₃H₇—n | 75 | 88–91/7 |
| a-vi | 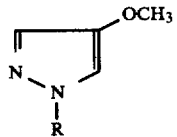 | 67 | 120/7 |
| a-vii | (H)— | | |
| a-viii | ▷— | | |
| a-ix | C₄H₉—n | 87 | 54/0,1 |
| a-x | C₄H₉—iso | 65 | 53/0,3 |
| a-xi | C₄H₉—tert. | 65 | 110–112/10 |
| a-xii | CH₂=CH—CH₂— | | |
| a-xiii | CH≡C—CH₂— | | |
| a-xiv | CH₃CH₂—O—CH₂—CH₂— | | |
| a-xv | 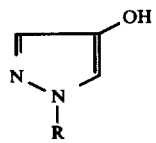 | | |

(b) The 4-hydroxy-pyrazoles to be used could be prepared, for example, as follows:

(b-i)

A solution of 22.4 g (0.2 mol) of 1-methyl-4-methoxy-pyrazole (for the preparation, see Archiv der Pharmazie 300 (1967), pages 704–708) in 100 ml of 48% strength hydrobromic acid was boiled under reflux for 9 hours. The excess acid was then distilled off in vacuo, the residue was dissolved in 40 ml of water and the solution was neutralized by adding solid sodium bicarbonate. The mixture was then extracted 6 times with 40 ml of chloroform each time, the combined extracts were dried over sodium sulphate and the solvent was distilled off in vacuo. 8.2 g (42% of theory) of 1-methyl-4-hydroxy-pyrazole remained in the form of pale yellow crystals with a melting point of 71° C.

The following compounds of the formula could be prepared in an analogous manner:

| Hydroxy Intermediate No. | R | Yield (% of theory) | Refractive index; melting point (°C.) |
|---|---|---|---|
| b-ii | C₂H₅ | 65 | $n_D^{20}$: 1.5078 |
| b-iii | C₃H₇—n | 91 | $n_D^{21}$: 1.5022 |
| b-iv | C₃H₇—iso | 75 | 63 |
| b-v | C₄H₉—sec. | 91 | $n_D^{21}$: 1.4994 |
| b-vi | (H)— | 62 | 79 |
| b-vii | (H)— | | |
| b-viii | ▷— | | |
| b-ix | C₄H₉—n | 88 | $n_D^{20}$: 1.5014 |
| b-x | C₄H₉—iso | 78 | 32 |
| b-xi | C₄H₉—tert. | 50 | 89 |
| b-xii | CH₂=CH—CH₂— | 73 | $n_D^{20}$: 1.5163 |
| b-xiii | CH≡C—CH₂— | | |
| b-xiv | CH₃CH₂—O—CH₂—CH₂— | 50 | $n_D^{21}$: 1.5015 |

| Hydroxy Intermediate No. | R | Yield (% of theory) | Refractive index; melting point (°C.) |
|---|---|---|---|
| b-xv |  | 76 | 122 |

(c) 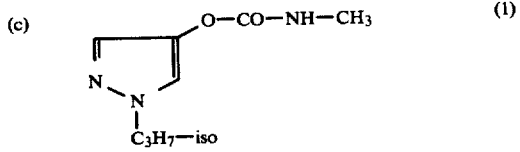 (1)

6 g (0.105 mol) of methyl isocyanate were added to a solution of 12.6 g (0.1 mol) of 1-isopropyl-4-hydroxy-pyrazole in 100 ml of acetone and 2 drops of triethylamine. The mixture was stirred at 45° C. for 12 hours and the solvent was then distilled off in vacuo. 17.4 g (95% of theory) of N-methyl-carbamic acid O-(1-iso-propyl-pyrazol-4-yl) ester were thus obtained in the form of beige crystals with a melting point of 40° C.

The following compounds of the formula

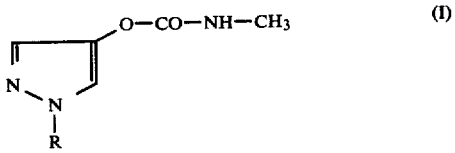 (I)

could be prepared analogously:

| Compound No. | R | Yield (% of theory) | Refractive index; melting point (°C.) |
|---|---|---|---|
| 2 | $C_2H_5$ | 77 | $n_D^{22}$: 1.4998 |
| 3 | $CH_3$ | 67 | 62 |
| 4 | $C_3H_7$—n | 90 | $n_D^{22}$: 1.4963 |
| 5 | $C_4H_9$—sec. | 79 | $n_D^{22}$: 1.4928 |
| 6 |  | 94 | 115 |
| 7 |  | | |
| 8 |  | | |
| 9 | $C_4H_9$—n | 93 | 51 |
| 10 | $C_4H_9$—iso | 93 | 80 |
| 11 | $C_4H_9$—tert. | 95 | 71 |
| 12 | $CH_2=CH-CH_2-$ | 95 | $n_D^{23}$: 1.5100 |
| 13 | $CH\equiv C-CH_2-$ | | |
| 14 | $CH_3-CH_2-O-CH_2-CH_2-$ | 98 | $n_D^{23}$: 1.4915 |
| 15 |  | 97 | 127 |

The pesticidal activity of the compounds of this invention is illustrated by the following examples wherein the compounds according to the present invention are each identified by the number (given in brackets) from the preparative examples hereinabove:

Example 2

Plutella test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (Brassica oleracea) were treated by being dipped into a preparation of active compound and were infested with caterpillars of the diamond-back moth (Plutella maculipennis), as long as the leaves were still moist.

After the specified periods of time, the degree of destruction was determined as a percentage: 100% meant that all of the caterpillars were killed whereas 0% meant that none of the caterpillars were killed.

In this test, for example, the following compounds showed a superior activity compared with the prior art: (3), (2), (4), (1), (5) and (6).

Example 3

Tetranychus test (resistant)

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (Phaseolus vulgaris) which were heavily infested with the two-spotted spider mite (Tetranychus urticae) in all stages of development were treated by being dipped into the preparation of the active compound.

After the specified periods of time, the degree of destruction was determined as a percentage: 100% meant that all of the spider mites were killed whereas 0% meant that none of the spider mites were killed.

In this test, for example, the following compounds showed a superior activity compared with the prior art: (5), (4) and (3).

Example 4

Test insect: Phaedon cochleariae larvae
Solvent: 3 parts by weight of acetone
Emulsifier: 1 part by weight of alkylaryl polyglycol ether To produce a suitable preparation of active compound, b 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil was decisive. The treated soil was filled into pots and these were planted with cabbage (Brassica oleracea). The active compound could in this way be taken up from the soil by the plant roots and be transported into the leaves.

To demonstrate the root-systemic effect, only the leaves were infested with the above-mentioned test insects after 7 days. After a further 2 days, the results were evaluated by counting or estimating the dead insects. The root-systemic action of the active compound was deduced from the destruction data. It was 100% when all of the test insects had been killed and 0% when just as many test insects were still alive as in the case of the untreated control.

In this test, for example, the following compound showed a superior action compared with the prior art: (1).

Example 5

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil was decisive. The treated soil was filled into pots, lettuce was sown in and the pots were kept at a greenhouse temperature of 27 degrees C.

After 4 weeks, the lettuce roots were examined for infestation with nematodes (root galls), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

In this test, for example, the following compound showed a superior activity compared with the prior art: (1).

Example 6

Test insects: *Aedes aegypti*
Number of test insects: 25
Solvent: Acetone

The active compound was dissolved in the solvent at a rate of 2 g per liter. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. The stated number of test animals was then placed in the Petri dish and the dish was covered with a glass lid.

The condition of the test insects was continuously observed. The time which was necessary for 100% "knockdown" was determined.

In this test, for example, the following compounds showed a superior action compared with the prior art: (2), (4), (1), (5) and (6).

It will be appreciated that the instant specification and examples are set forth by way of illustration and not limitation, and that various modifications and changes may be made without departing from the spirit and scope of the present invention.

What is claimed is:

1. An N-methyl-carbamic acid O-pyrazol-4-yl (1-substituted)-ester of the formula

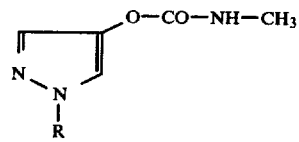

in which R is alkyl, alkenyl, alkinyl or alkoxyalkyl with up to 4 carbon atoms, or cycloalkyl with 3 to 6 carbon atoms.

2. A compound according to claim 1, wherein such compound is N-methyl-carbamic acid O-(1-iso-propyl-pyrazol-4-yl) ester of the formula

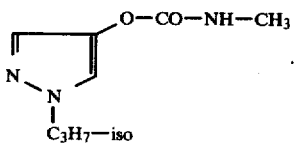

3. A compound according to claim 1, wherein such compound is N-methyl-carbamic acid O-(1-n-propyl-pyrazol-4-yl) ester of the formula

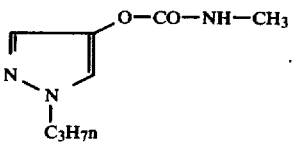

4. A compound according to claim 1, wherein such compound is N-methyl-carbamic acid O-(1-sec.-butyl-pyrazol-4-yl) ester of the formula

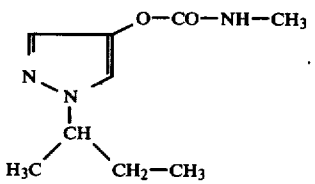

5. A compound according to claim 1, wherein such compound is N-methyl-carbamic acid O-(1-tert.-butyl-pyrazol-4-yl) ester of the formula

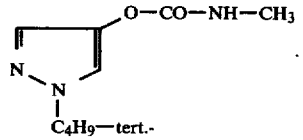

6. A compound according to claim 1, wherein such compound is N-methyl-carbamic acid O-(1-allyl-pyrazol-4-yl) ester of the formula

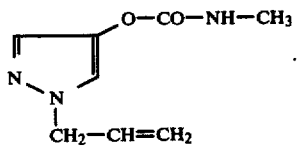

7. An insecticidal, acaricidal or nematicidal composition comprising an insecticidally, acaricidally or nematicidally effective amount of a compound according to claim 1 in admixture with a diluent.

8. A method of combating insects, acarids or nematodes comprising applying to the insects, acarids or nematodes, or to a habitat thereof, an insecticidally, acaricidally or nematicidally effective amount of a compound according to claim 1.

9. The method according to claim 8, wherein such compound is N-methyl-carbamic acid O-(1-iso-propyl-pyrazol-4-yl) ester, N-methyl-carbamic acid O-(1-n-propyl-pyrazol-4-yl) ester N-methyl-carbamic acid O-(1-sec.butyl-pyrazol-4-yl) ester N-methyl-carbamic acid O-(1-tert.-butyl-pyrazol-4-yl) ester, or N-methyl-carbamic acid O-(1-allyl-pyrazol-4-yl) ester, and it is applied to a domesticated animal to free the animal from parasites.

* * * * *